(12) United States Patent
Viavattine et al.

(10) Patent No.: US 12,102,832 B2
(45) Date of Patent: Oct. 1, 2024

(54) FOLDED HEADSPACE INSULATOR

(71) Applicant: Medtronic, Inc., Minneapolis, MN (US)

(72) Inventors: Joseph J. Viavattine, Vadnais Heights, MN (US); Christopher T. Stockton, Bloomington, MN (US); Hailiang Zhao, Plymouth, MN (US); Timothy T. Bomstad, Bigfork, MN (US); Jude M. Mallawaaratchy, Rosemount, MN (US); George Patras, Greenfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 190 days.

(21) Appl. No.: 17/324,556

(22) Filed: May 19, 2021

(65) Prior Publication Data
US 2022/0370811 A1  Nov. 24, 2022

(51) Int. Cl.
| | |
|---|---|
| *H01M 50/528* | (2021.01) |
| *A61N 1/375* | (2006.01) |
| *H01M 50/169* | (2021.01) |
| *H01M 50/179* | (2021.01) |

(52) U.S. Cl.
CPC ....... *A61N 1/37512* (2017.08); *A61N 1/3758* (2013.01); *H01M 50/179* (2021.01); *H01M 50/528* (2021.01); *H01M 50/169* (2021.01)

(58) Field of Classification Search
CPC ............. H01M 50/169; H01M 50/179; H01M 50/528; Y02E 60/10
See application file for complete search history.

(56) References Cited

U.S. PATENT DOCUMENTS

| | | | |
|---|---|---|---|
| 6,402,793 B1* | 6/2002 | Miltich | A61N 1/3968 361/522 |
| 7,927,738 B2 | 4/2011 | Howard et al. | |
| 8,053,106 B1* | 11/2011 | Pal | H01M 50/147 429/175 |
| 2005/0112460 A1* | 5/2005 | Howard | H01M 6/16 429/72 |

(Continued)

FOREIGN PATENT DOCUMENTS

KR 20150115435 A * 10/2015

OTHER PUBLICATIONS

Omnexus, "Thermal Insulation", https://omnexus.specialchem.com/polymer-properties/properties/thermal-insulation retrieved from https://archive.org Date: Nov. 14, 2023 (Year: 2016).*

(Continued)

*Primary Examiner* — Matthew T Martin
*Assistant Examiner* — Jared Hansen
(74) *Attorney, Agent, or Firm* — Mueting Raasch Group (57) ABSTRACT

A battery comprising a tubular battery housing having a first end and a second end. The first end and the second end can have a substantially same inner diameter and a substantially same outer diameter. The battery further comprises a battery cell within the tubular battery housing. The battery further comprises a top battery cover coupled to the first end and a bottom battery cover coupled to the second end to form a substantially sealed enclosure around the battery cell. Method for manufacturing the battery are also described.

17 Claims, 8 Drawing Sheets

(56) References Cited

U.S. PATENT DOCUMENTS

| | | | | |
|---|---|---|---|---|
| 2008/0008931 | A1* | 1/2008 | Howard | H01M 50/636 |
| | | | | 429/129 |
| 2008/0233474 | A1* | 9/2008 | Son | H01M 50/147 |
| | | | | 429/185 |
| 2012/0015243 | A1* | 1/2012 | Han | H01M 50/103 |
| | | | | 429/185 |
| 2012/0160559 | A1* | 6/2012 | Tsutsumi | H01G 11/66 |
| | | | | 174/551 |
| 2013/0288092 | A1* | 10/2013 | Nidelkoff | H01M 10/0587 |
| | | | | 429/94 |
| 2014/0272548 | A1* | 9/2014 | Woo | H01M 10/052 |
| | | | | 429/174 |

OTHER PUBLICATIONS

KR20150115435A, Park, et al. "Secondary Battery", machine English translation retrieved from https://worldwide.espacenet.com/ Date: May 22, 2024 (Year: 2015).*

* cited by examiner

FOLDED HEADSPACE INSULATOR

FIELD

The present technology is generally related to batteries for use with implantable medical devices. More specifically, the present technology relates to cover insulators for tubular batteries.

BACKGROUND

As implantable medical device (IMD) technology advances, issues such as IMD battery longevity, IMD size and shape, IMD mass, and patient comfort remain key considerations in the IMD design process. Battery size and capacity, for example, significantly impact the physical configuration of the IMD and the duration of service time within the patient before battery replacement or recharge is required. Batteries can include insulators to provide electrical insulation. However, insulators can shift position and thereby leave internal components vulnerable to outside forces or to electrical shorts.

SUMMARY

The techniques of this disclosure generally relate to battery apparatuses.

In one aspect, the present disclosure provides a battery having a battery cell within a battery housing. The battery further comprises a headspace insulator inserted between the battery cell and a top cover. The headspace insulator includes an upper insulator portion, a lower insulator portion, and a neck joining the upper insulator portion and the lower insulator portion.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The batteries described herein may be used in any suitable device, such as an implantable medical device. Examples of suitable implantable medical devices include implantable devices that provide therapy to, or sense signals from, a heart of a patient; implantable devices that provide therapy to, or sense signals from, a portion of a central or peripheral nervous system of a patient, implantable devices that deliver therapeutic fluids to a patient, and the like. More specific examples of implantable medical devices that may employ batteries as described herein include implantable pacemakers, cardioverters, defibrillators, deep brain stimulators, spinal cord stimulators, and drug pumps. For purposes of context, an implantable cardiac device (ICD) is discussed regarding FIGS. 1-2 below.

Figure 1:
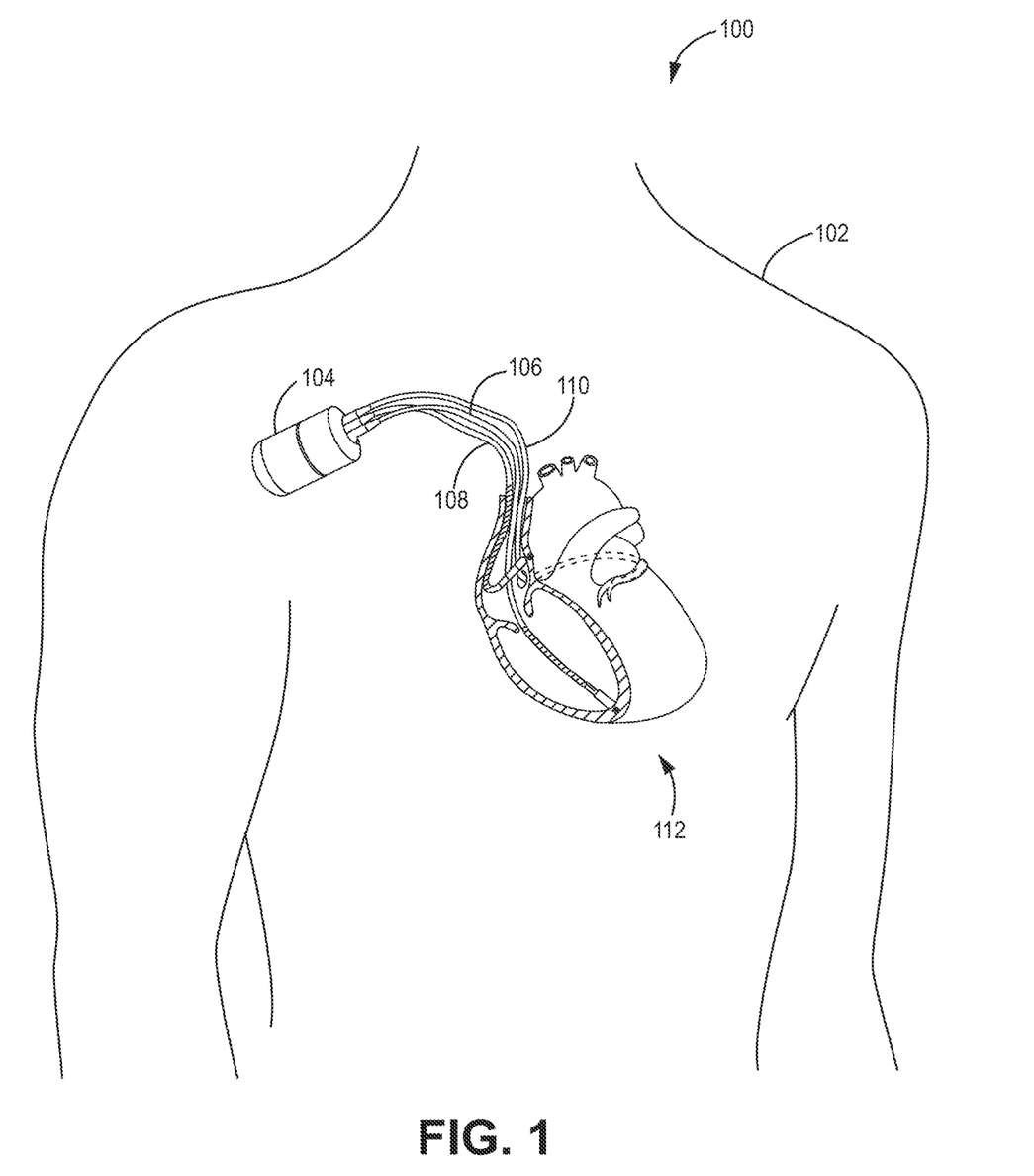
FIG. 1 is a diagram of an example therapy system including an implantable cardiac device (ICD).

FIG. 1 is a conceptual diagram illustrating an example system 100 that provides therapy to patient 102. Therapy system 100 includes ICD 104, which is connected to leads 106, 108 and 110. ICD 104 may be, for example, a device that provides cardiac rhythm management therapy to heart 112, and may include, for example, an implantable pacemaker, cardioverter, and/or defibrillator that provide therapy to heart 112 of patient 102 via electrodes coupled to one or more of leads 106, 108 and 110. Leads 106, 108, 110 extend into the heart 112 of patient 102 to sense electrical activity of heart 112 and/or deliver electrical stimulation to heart 112.

Figure 2:
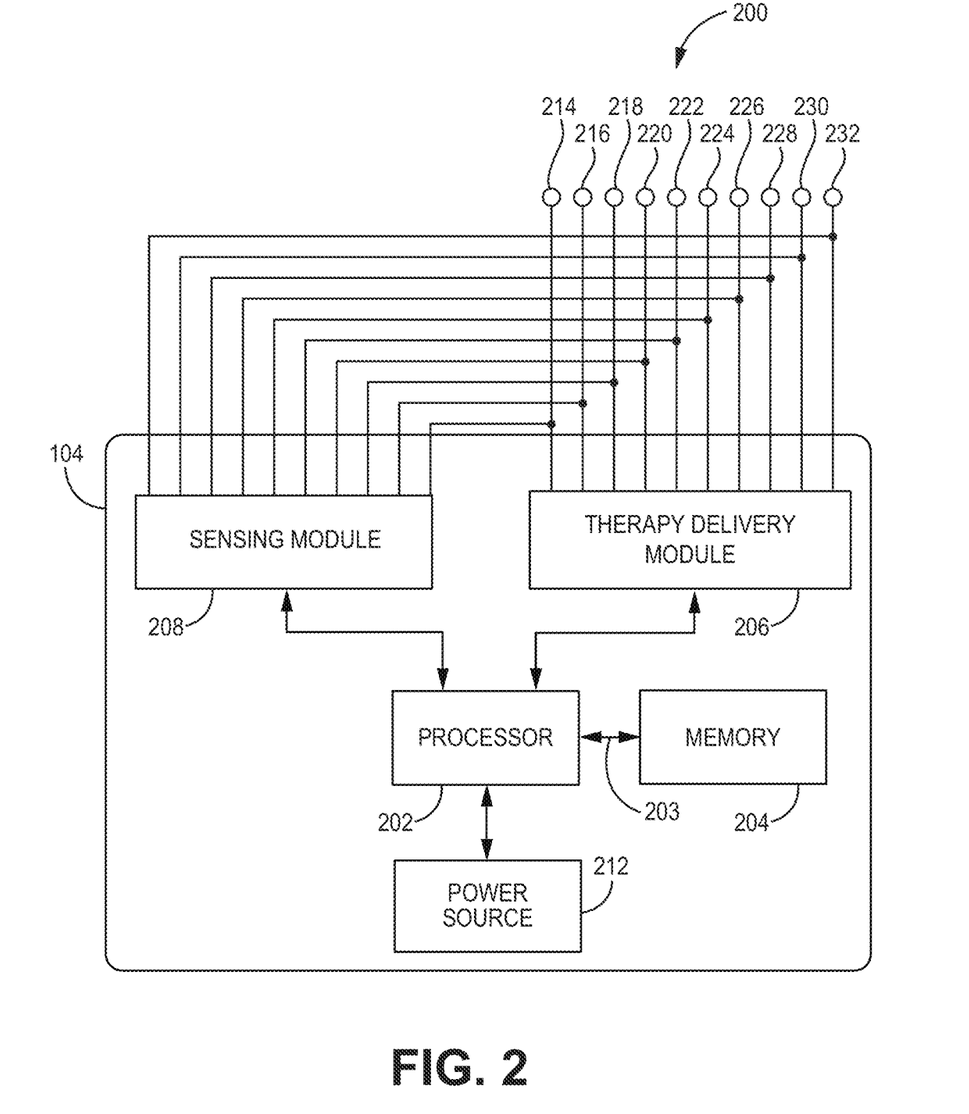
FIG. 2 is a block diagram of an ICD that includes a battery in accordance with embodiments.

FIG. 2 is a block diagram of an ICD 104 that includes a power source 212 comprising a battery in accordance with embodiments. The ICD 200 includes a processor 202, memory 204, stimulation generator 206, sensing module 208, and power source 212. The processor 202 may communicate with memory 204 over an interconnect 203 (e.g., a bus). The interconnect 203 may include any number of technologies, including industry standard architecture (ISA), extended ISA (EISA), peripheral component interconnect (PCI), peripheral component interconnect extended (PCIx), PCI express (PCIe), or any number of other technologies. The interconnect 203 may be a proprietary bus.

Stimulation generator 206 is electrically coupled to electrodes 214, 216, 218, 220, 222, 224, 226, 228, 230, 232 e.g., via conductors of the respective lead 106, 108, 110, or, in the case of housing electrode 230, via an electrical conductor disposed within housing of ICD 104. Stimulation generator 206 is configured to generate and deliver electrical stimulation therapy to heart 112 to manage a rhythm of heart 112. Electrodes 214, 216, 218, 220, 222, 224, 226, 228, 230, 232 can include ring electrodes or helical electrodes, for example, although embodiments are not limited thereto. Sensing module 208 monitors signals from at least one of electrodes 214, 216, 218, 220, 222, 224, 226, 228, 230, 232 to monitor electrical activity of heart 112, e.g., via an EGM signal.

The various components of ICD 104 are coupled to power source 212, which may include a rechargeable or non-rechargeable battery. For example, the processor 202 may be coupled to receive power from the power source 212. A non-rechargeable battery may be selected to last for several years, while a rechargeable battery may be inductively charged from an external device, e.g., on a daily or weekly basis. Examples of a rechargeable battery include, but are not limited to, a lithium-ion battery, a lithium/silver vanadium oxide battery, a lithium polymer battery, or a supercapacitor.

Figure 3A:
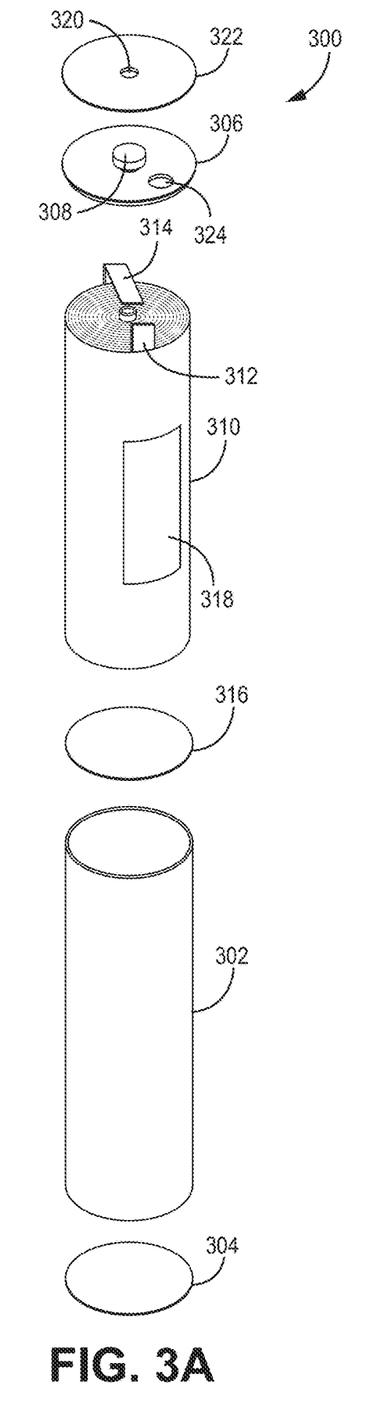
FIG. 3A is an exploded view of battery components in accordance with embodiments.

FIG. 3A is an exploded view of battery 300 components in accordance with embodiments. Power source 212 may include a battery housing 302. The battery housing 302 can comprise metallic alloys and provide the ground or negative terminal of a battery 300. Alternatively, the battery housing 302 can be at a positive potential and a feedthrough 308 (described in more detail later herein) can be at negative potential.

The battery housing 302 can have an open first end and an open second end and the battery housing 302 can be substantially cylindrical having a uniform inner diameter, a uniform outer diameter and uniform wall thickness throughout a length of the battery housing 302. While the battery housing 302 is shown and described as having a generally cylindrical shape, however, the battery housing 302 can have other cross-sectional shapes including, but not limited to rectangular, triangular, square, hexagonal, and octagonal shapes. As referred to herein, the term tubular does not indicate to any particular cross-sectional shape, but only indicates a component including a hollow elongated body.

Figure 3B:
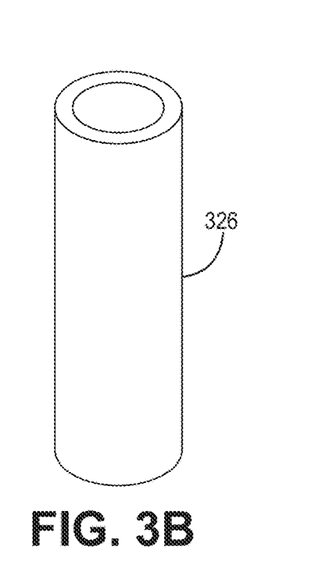
FIG. 3B is a view of an alternative battery housing in accordance with embodiments.

Alternatively, a battery housing 326 can be formed in a deep draw process in which the one of the first end and second end is closed and the corresponding cover is instead formed as one piece with the battery housing 326, as shown in FIG. 3B. Other components of FIG. 3A can be included within the one-piece battery housing 326, including, for example, battery cell 310 and other components.

The battery housing 302 can have a length greater than its diameter. As examples, the length of the battery housing 302 can be about 1.1 times to about 10 times the diameter of the battery housing 302. As an example, the length of the battery housing 302 can be about 50-70 millimeters and the diameter of the battery housing can be about 15-25 millimeters. In examples, the battery housing 302 can be about 65 millimeters in length and about 19 millimeters in diameter.

The battery housing 302 having an open first end and an open second end can be formed by any suitable process. For example, the battery housing 302 can be formed by extruding or rolling and seam sealing, which removes the need for drying or other processes associated with deep drawing. The battery housing 302 can be formed in a machining process from a solid base stock. The battery housing 302 can be formed from a drawn tubing. Shrink wrapping or other surface can be provided over the battery housing 302. The shrink wrapping can prevent electrical shorting and provide an insulator for the battery. The shrink wrapping can be heat shrunk to the outer surface of the battery housing 302. In some examples, such a shrink wrapping can be applied around the battery 300 after assembly.

The bottom cover 304 may be coupled to the battery housing 302 in any suitable manner. For example, the bottom cover 304 may be coupled to the battery housing by welding. The battery 300 can include a top cover 306. The top cover 306, the bottom cover 304, and the battery housing 302 may have any suitable thicknesses and can be the same or different. In some examples, walls of a battery housing 302 can be about 0.008 to 0.016 inches (or 0.2 to 0.4 millimeters) thick. In some examples, the top cover 306 can be about 0.5 inches (or 12.7 millimeters) thick. The top cover 306 can include feedthrough 308 to provide electrical contact to the battery cell 310. The top cover 306 can be made thinner if feedthrough 308 is not integrated into the top cover 306. For example, the top cover 306 can be about 0.008 to 0.07 inches (or 0.2 to 1.778 millimeters) thick in absence of a feedthrough. The bottom cover 304 can be about 0.008-0.04 inches (or 0.2 to 1.016 millimeters) thick. In examples, the bottom cover 304 can be thinner than the walls of the battery housing 302. The top cover 306, the bottom cover 304, and the battery housing 302 can all be of same thicknesses as each other in some embodiments. In some embodiments, any of the top cover 306, the bottom cover 304 and the battery housing 302 can be thinner or thicker than any other of the top cover 306, bottom cover 304 and battery housing 302. This allows for independent design of each of the top cover 306, bottom cover 304 and battery housing 302.

Similarly to the battery housing 302, the top cover 306, and bottom cover 304 can comprise metallic alloys and provide the ground or negative terminal of the tubular battery. Alternatively, the battery housing 302 can be at positive potential with the feedthrough 308 being at negative potential. The battery housing 302 can be welded to bottom cover 304 and top cover 306 or otherwise attached to form a substantially-sealed enclosure encasing battery cell 310.

Battery cell 310 is depicted as being arranged in a jelly roll configuration with tabs 312 and 314, although embodiments are not limited to a jelly roll configuration for battery cell 310. In a jelly roll configuration, an insulating sheet (not shown in FIG. 3A) is laid down, then a thin layer (not shown in FIG. 3A) of an anode material is laid down, a separator layer is applied, and a cathode material is layered (not shown in FIG. 3A) on top. The layers are rolled and inserted into battery housing 302. A bottom insulator 316 can prevent the battery cell 310 from touching or contacting the bottom cover 304. In an example, one tab 312 may connect to cathode material, and the other tab 314 may connect to anode material of the battery cell 310. Battery cell 310 may comprise lithium/silver vanadium oxide, for example. Alternatively, battery cell 310 can be rechargeable and anodes and cathodes can comprise other materials besides lithium/silver vanadium oxide. Adhesive tape 318 can be included to hold the outer edge of the jelly roll in place.

Top cover 306 includes feedthrough 308 to provide electrical contact to the battery cell 310 through opening 320. Insulator 322 is applied over the top cover 306. Opening 324 allows access for an electrolyte to be provided to the battery cell 310 before the top cover 306 is welded or otherwise attached to the battery housing 302. In some examples, as mentioned earlier herein with reference to FIG. 3A, shrink wrapping can be applied over the entire battery 300.

Figure 4:
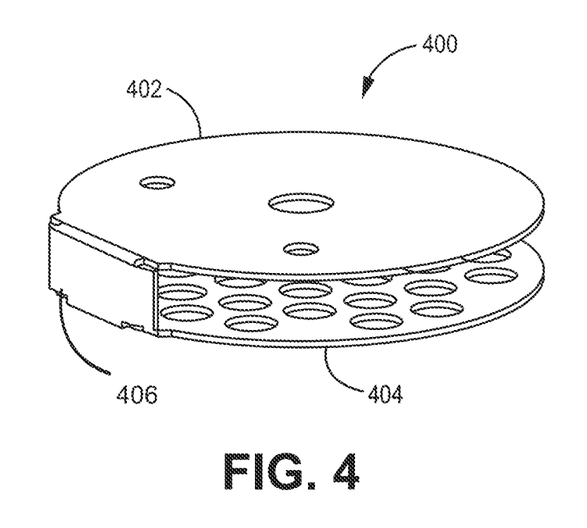
FIG. 4 is a perspective view of a headspace insulator to illustrate fitting of the headspace insulator within battery components in accordance with embodiments.

FIG. 4 is a perspective view of a headspace insulator 400 that can be inserted between the battery cell 310 and top cover 306 to retain the battery cell 310 in accordance with embodiments. The headspace insulator 400 can perform functions including isolating the battery cell 310 from the battery housing 302, providing mechanical stability for the battery cell 310, preventing electrical shorts, providing thermal insulation for the battery cell 310, or allowing electrolyte to pass through the insulators to initially fill the battery cell 310, among other functions. The headspace insulator 400 can include an upper insulator portion 402 and a lower insulator portion 404. The upper insulator portion 402 can be located over feedthrough 308. In some examples, the headspace insulator 400 can include a neck 406 joining the upper insulator portion 402 and the lower insulator portion 404. The headspace insulator 400 can be manufactured through any suitable process including laser cutting, die stamping, injection molding, 3D printing, etc. The headspace insulator 400 can comprise any suitable electrically insulating material or thermally insulating material, including but not limited to plastic-based and polymer-based materials including ethylene tetrafluoroethylene (ETFE), polypropylene, polyurethane, fluoropolymers, polyethylene, polyimide, etc.

The headspace insulator 400 can provide functions of the insulator 322 and other functions. FIGS. 5-9 include further details regarding the headspace insulator 400.

Figure 5:
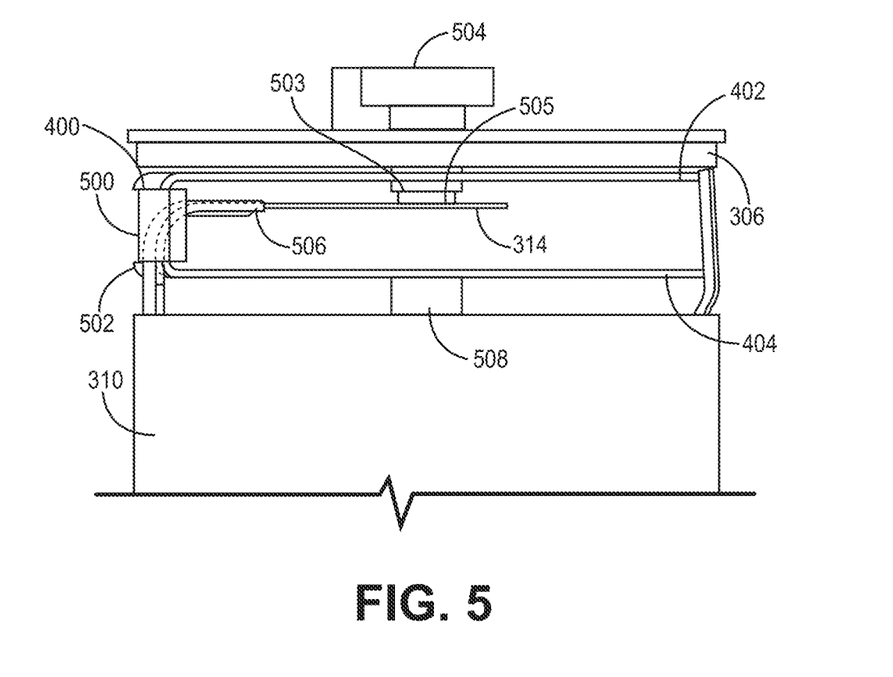
FIG. 5 is a side view of a portion of a battery including a headspace insulator in accordance with embodiments.

FIG. 5 is a side view of a portion of a battery including a headspace insulator 400 in accordance with embodiments.

Upper insulator portion 402 and lower insulator portion 404 are shown. A hinge portion, or neck 500 can join the upper insulator portion 402 to the lower insulator portion 404. The neck 500 can retain the lower insulator portion 404 against the battery cell 310 in place by exerting a compressive force to prevent or reduce battery cell 310 movement. The neck 500 further displaces the tab 314 from the battery case (not shown in FIG. 5) and accommodates the tab 314 within a neck opening 502 to provides thermal insulation for the tab 314. The tab 314 can be a positive battery tab or a negative tab. The neck opening 502 can also allow the neck 500 to extend behind the tab 314. Tape 506 (or another attachment or insulation mechanism) can be provided around at least a portion of the tab 314. In some embodiments, the tape 506 can be provided on the tab 314 throughout a portion of the tab 314 that extends into the battery cell 310. In some embodiments, the tape 506 can extend along some or part of the battery cell 310 The tab 314 can extend toward inwardly from the neck 500, toward the feedthrough assembly 504 and the tab 314 can be suitably connected, for example by welding, to the feedthrough assembly 504. The feedthrough assembly 504 can include a ferrule 503 and a feedthrough pin 505.

In some examples, when the headspace insulator 400 is in place, subsequent to welding or otherwise attaching the tab 314, the headspace insulator 400 (e.g., the upper insulator portion 402) can support top cover 306 to reduce or eliminate mechanical stress to the tab 314. In some examples, the upper insulator portion 402 can reduce stress at the tab 314 that can be created by the feedthrough assembly 504. Central mandrel portion 508 can provide a standoff between a top portion of battery cell 310 and the lower insulator portion 404. Similarly, mandrel portion 508 can provide a standoff at a lower portion of battery cell 310 (not shown). Central mandrel portion 058 can keep portions of the battery cell 310 (for example, electrodes and separator) from being compressed on their ends during assembly or manufacturing processes.

Figure 6:
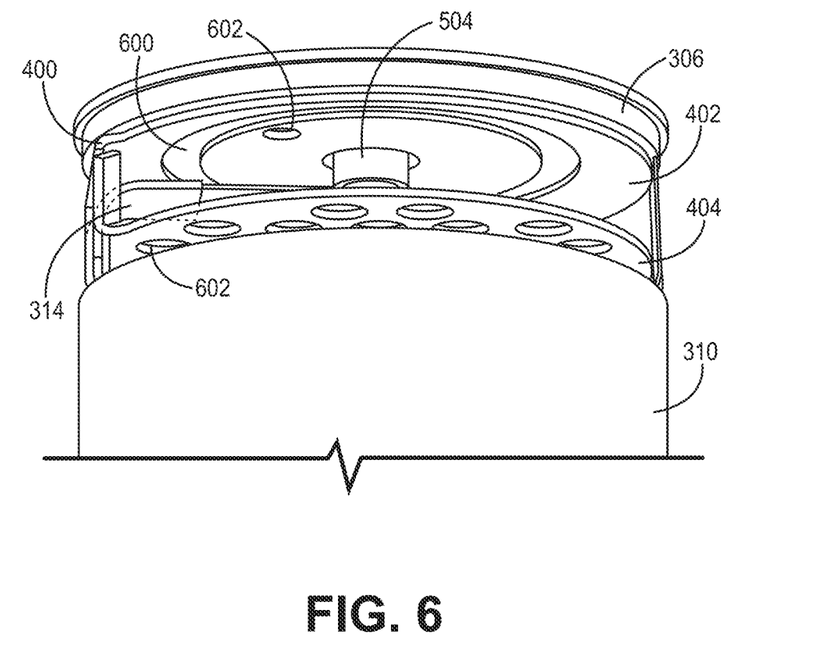
FIG. 6 is a rotated side view of a portion of a battery including a headspace insulator in accordance with embodiments.

FIG. 6 is a rotated side view of a portion of a battery including a headspace insulator 400 in accordance with embodiments. An opening 600 can provide access for providing electrolyte to the battery cell 310. Openings 602 are provided in at least one of the upper insulator portion 402 and lower insulator portion 404 through which electrolyte can pass to the battery cell 310. The openings 602 can be of other shapes, including slits, hexagonal, oval, etc., and can be of uniform size or different sizes. The openings 602 can form symmetrical or asymmetrical patterns. In embodiments, the openings will be positioned and sized to be sufficiently large (for example 0.03 inches-0.25 inches) to allow electrolyte to reach the battery cell 310 but sufficiently small such that the tab 314 cannot fit through openings 602, to prevent shorting between the tab 314 and top cover 306.

Figures 7A, 7B:
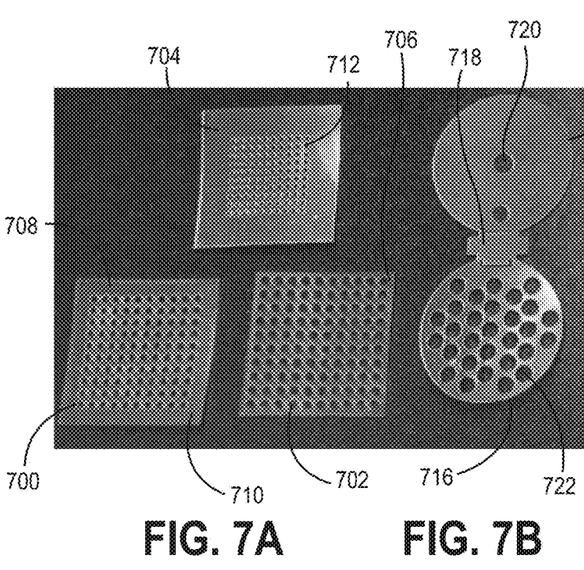
FIGS. 7A-7I illustrate alternative surface features and hinging mechanisms for insulator portions in accordance with embodiments.

FIGS. 7A-7I illustrate alternative surface features and hinging mechanisms for insulator portions in accordance with embodiments. As can be seen in FIG. 7A-7I, insulator portions can be of a variety of shapes, including at least square and circular shapes, with different numbers and sizes of openings. FIG. 7A depicts square insulator portions 700, 702 and 704. Square insulator portion 702 can include a greater number of openings 706. Square insulator portion 700 can include a larger amount of space 708 around openings 710; for example, square insulator portion can include openings 710 over a smaller area than does insulator portion 702. Square insulator portion 704 can include openings 712 over a smaller area than does square insulator portion 700.

Figure 7C:
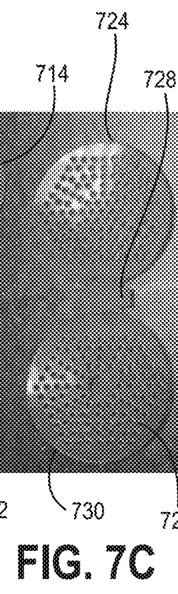

FIG. 7B illustrates a first insulator portion 714 and a second insulator portion 716 connected by a hinge portion 718. The first insulator portion 714 can include one or two openings 720 for introducing electrolyte to the battery cell of a battery. Openings 722 can be included on the second insulator portion 716 in a circular shape or any other shape. FIG. 7C illustrates a first insulator portion 724 and second insulator portion 726 connected by a hinge portion 728. The first insulator portion 724 and the second insulator portion 726 can include a same or similar number of openings 730 arranged in a circular configuration with no or little space between the openings 730 and edges of respective first insulator portion 724 and second insulator portion 726.

Figure 7D:
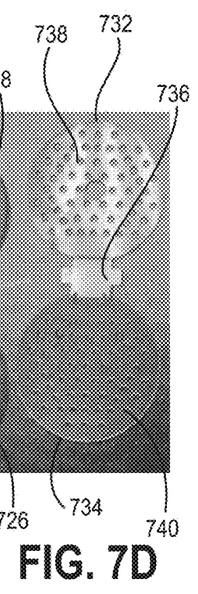
Figures 7E, 7F:
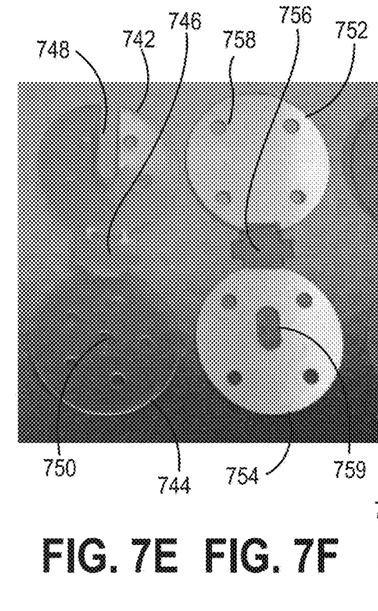

FIG. 7D illustrates a first insulator portion 732 and a second insulator portion 734 connected by a hinge portion 736. First insulator portion 732 can include a fewer number of openings 738 and the openings 738 can be larger than openings 740 on the second insulator portion 734. FIG. 7E illustrates a first insulator portion 742 and a second insulator portion 744, connected by a hinge portion 746. The first insulator portion 742 can include a slit 748 or similar feature shaped to accommodate, for example, a tab (e.g., a positive tab or a negative tab) similar to the tab 314 (FIGS. 3-6). Feature 750 can accommodate, for example, a standoff portion 508 (FIG. 5).

Figures 7G, 7H:
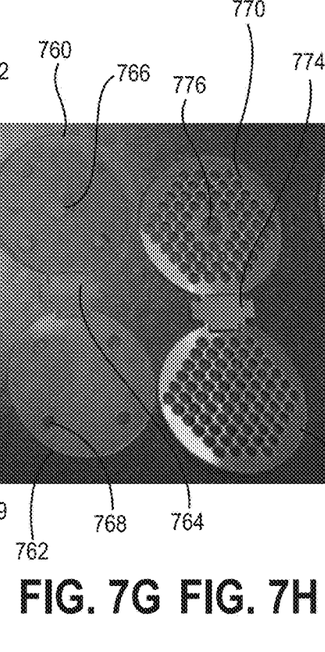

FIG. 7F illustrates a first insulator portion 752 and a second insulator portion 754 connected by a hinge portion 756. The first insulator portion 752 and the second insulator portion 754 can include a similar number of openings 758 of similar size. The second insulator portion 754 can include a feature 759 to accommodate, for example, a standoff portion 508 (FIG. 5). FIG. 7G is similar to FIG. 7F in that a first insulator portion 760 and a second insulator portion 762 are illustrated as connected by a hinge portion 764. The first insulator portion 760 and the second insulator portion 762 can include a similar number of openings 768. The first insulator portion 760 can include a feature 766 to accommodate, for example, a feedthrough assembly 504 (FIGS. 5-6)

Figure 7I:
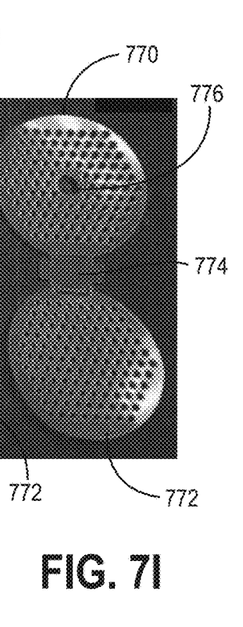

FIG. 7H and FIG. 7I illustrate a first insulator portion 770 and a second insulator portion 772 connected by a hinge portion 774. The insulator portion 770 in FIG. 7H and FIG. 7I each can include a feature 776 to accommodate a feedthrough assembly 504 (FIGS. 5-6) or portion thereof. FIG. 7H shows openings in each of the first insulator portion 770 and second insulator portion 772 of a first size, while FIG. 7I depicts openings of a second size smaller than the first size.

Figure 8:
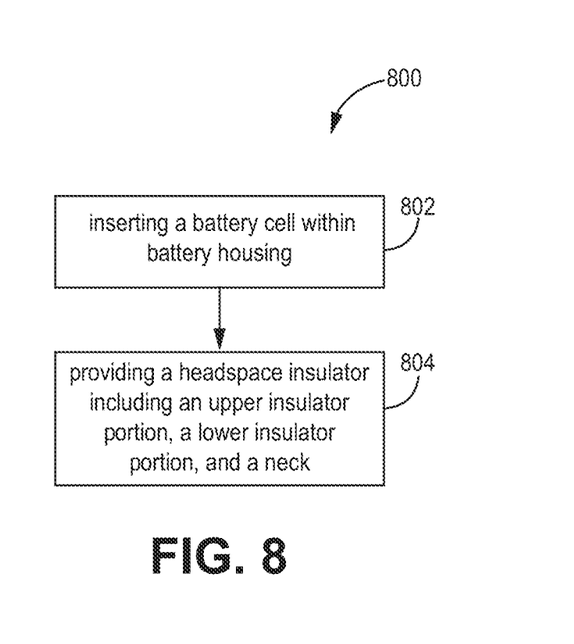
FIG. 8 is a flow diagram of a method for manufacturing a battery in accordance with embodiments.

FIG. 8 is a flow diagram of a method 800 for manufacturing a battery 300 in accordance with embodiments. Reference is made to elements of the battery 300 described above with reference to FIGS. 3-7. The method 800 can begin with operation 802 with inserting a battery cell 310 within a battery housing 302. As described earlier herein, the battery housing 302 can be open on one or both ends, and formed in a deep draw process or other process.

The method 800 can continue with operation 804 with providing a headspace insulator 400 disposed between the battery cell 310 and a top cover 306, the headspace insulator 400 including an upper insulator portion 402, a lower insulator portion 404, and a neck 500 joining the upper insulator portion 402 and the lower insulator portion 404. The neck 500 can include a neck opening 502 within the neck. A battery tab 314 can be at least partially encased within the neck opening 502.

The method 800 can further include welding a top cover 306 to the headspace insulator 400 at the first end. The method 800 can further include providing electrolyte to the battery cell through an opening 602 of the upper insulator portion 402. At least one of the upper insulator portion 402 and the lower insulator portion 404 can be manufactured using laser cutting, stamping, injection molding, 3D printing, or another process.

Various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Accordingly, the term "processor" as used herein may refer to any of the foregoing structure or any other physical structure suitable for implementation of the described techniques. Also, the techniques could be fully implemented in one or more circuits or logic elements.

What is claimed is:

1. A battery comprising:
   a battery cell within a battery housing; and
   a headspace insulator inserted between the battery cell and a top cover, the headspace insulator including an upper insulator portion, a lower insulator portion, and a neck joining the upper insulator portion and the lower insulator portion, wherein the upper insulator portion comprises a first planar surface and a second planar surface, wherein the neck exerts a compressive force against the lower insulator portion to retain the lower insulator portion against the battery cell, wherein the upper insulator portion includes a first plurality of openings and the lower insulator portion includes a second plurality of openings, wherein the first and the second plurality of openings are configured to provide electrolyte to the battery.

2. The battery of claim 1, wherein the neck includes a neck opening for accommodating a battery tab of the battery.

3. The battery of claim 2, wherein the neck opening accommodates a positive battery tab of the battery.

4. The battery of claim 2, wherein the neck opening accommodates a negative battery tab of the battery.

5. The battery of claim 2, wherein the neck displaces the battery tab from the battery housing.

6. The battery of claim 2, further comprising an insulation tape disposed on at least a portion of the battery tab.

7. The battery of claim 1, wherein the headspace insulator is comprised of electrically and thermally insulating material.

8. The battery of claim 1 wherein the lower insulator portion comprises a lower first planar surface and a lower second planar surface, wherein the lower first planar surface and the lower second planar surface are parallel to the first planar surface and the second planar surface.

9. The battery of claim 8, wherein the neck joins the upper insulator portion to the lower insulator portion along a perimeter of the upper insulator portion and a perimeter of the lower insulator portion.

10. The battery of claim 1, wherein the neck comprises a hinge.

11. The battery of claim 1, wherein the upper insulator portion is movable relative to the lower insulator portion about the neck.

12. The battery of claim 1, wherein a number of the first plurality of openings is different from a number of the second plurality of openings.

13. The battery of claim 1, wherein a number of the first plurality of openings is equal to a number of the second plurality of openings.

14. The battery of claim 1, wherein one or both of the first plurality of openings and the second plurality of openings forms a symmetrical pattern.

15. The battery of claim 1, wherein one or both of the first plurality of openings and the second plurality of openings forms an asymmetrical pattern.

16. The battery of claim 1, wherein a size of the first and the second plurality of openings is between 0.03 inches to 0.25 inches.

17. The battery of claim 2, wherein a size of the first and the second plurality of openings is sufficiently small so that the battery tab cannot fit through any of the first and the second plurality of openings.

* * * * *